United States Patent [19]

O'Lenick, Jr.

[11] Patent Number: 5,488,121
[45] Date of Patent: Jan. 30, 1996

[54] DI-GUERBET ESTERS

[75] Inventor: Anthony J. O'Lenick, Jr., Lilburn, Ga.

[73] Assignee: Siltech Inc., Norcross, Ga.

[21] Appl. No.: 332,135

[22] Filed: Oct. 31, 1994

[51] Int. Cl.$^6$ .................................................. C07C 3/100
[52] U.S. Cl. .................................................. 554/167
[58] Field of Search ............................................ 554/167

[56] References Cited

U.S. PATENT DOCUMENTS

| | | | |
|---|---|---|---|
| 4,114,183 | 3/1979 | Koch et al. | 252/56 S |
| 4,425,458 | 1/1984 | Lindner et al. | 524/314 |
| 4,868,236 | 9/1989 | O'Lenick | 524/308 |
| 5,011,629 | 4/1991 | Bilbo et al. | 260/405 |

*Primary Examiner*—José G. Dees
*Assistant Examiner*—Deborah D. Carr

[57] ABSTRACT

The present invention deals with the certain novel di-guerbet esters which are prepared by the reaction of a guerbet alcohol and a guerbet acid. These materials are useful as lubricating oils where outstanding liquidity, resistance to oxidation, and minimal variation in viscosity as a function of temperature is required. This combination of properties make these compounds excellent candidates as additives to synthetic lubricating oil and extreme pressure additives.

10 Claims, No Drawings

DI-GUERBET ESTERS

BACKGROUND OF THE INVENTION

1. Field of the Invention

The present invention deals with the certain novel di-guerbet esters which are prepared by the reaction of a guerbet alcohol and a guerbet acid. These materials are useful as lubricating oils where outstanding liquidity, resistance to oxidation, and minimal variation in viscosity as a function of temperature is required. This combination of properties make these compounds excellent candidates as additives to synthetic lubricating oil and extreme pressure additives.

2. Description of the Art Practices

Guerbet alcohols have been known for many years. Over the years there have been a number of derivatives patented. U.S. Pat. No. 4,868,236 to O'Lenick discloses a guerbet citric ester and polymers thereof useful in plastic lubrication.

U.S. Pat. No. 4,425,458 to Lindner and O'Lenick teaches that specific guerbet esters can be used as polycarbonate lubricants.

None of these materials possess the critical di-guerbet linkage in the molecule. That is the molecules of the current invention have guerbet substitution patterns on both the alcohol and acid portion of the molecule and contain no ether linkages.

THE INVENTION

This invention relates to a particular group of highly branched esters made by the reaction of a guerbet alcohol and a guerbet acid. Additional aspects of the invention is the application of these materials as lubricating oils were the specific di-branching properties of an ester having guerbet derived branching on both the acid and alcohol portion of the molecule result in superior liquidity, lubricity, improved viscosity index modification and oxidative stability.

The compounds of the current invention are specific di beta branched esters conforming to the following structure;

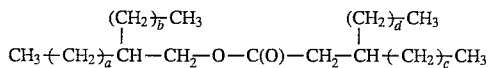

wherein a, b, c and d are independently integers ranging from 4 to 20.

Preferred Embodiment

In a preferred embodiment a, c and d are each 3.

In another preferred embodiment a, b, c and d are each 4.

In another preferred embodiment a, b, c and d are each 5.

In another preferred embodiment a, b c and d are each 6.

In another preferred embodiment a, b, c and d are each 7.

In another preferred embodiment a, b, c and d are each 14.

In still another preferred embodiment a and b are 14, and c and d are 3.

In still another preferred embodiment a and b are 8 and c and d are 4.

In still another preferred embodiment a and b are 7 and c and d are 5.

In still another preferred embodiment a and b are 5 and c and d are 8.

In still another preferred embodiment a and b are 4 and c and d are 8.

In still another preferred embodiment a and b are 3, and c and d are 14.

EXAMPLES

RAW MATERIALS

Guerbet Alcohols

Guerbet Alcohols are regiospecifically beta branched alcohols. They have been known since the 1890's when Marcel Guerbet first synthesized them. (M. Guerbet, C. R. Acad. Sci. Paris, 128, 511; 1002 (1899)). These materials are high in molecular weight and are liquid to very low temperatures. The guerbet reaction gives very specific branching in the alcohol as shown;

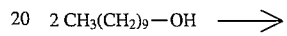

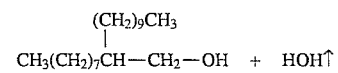

As can be seen by the above reaction the molecules have substitution on the second carbon from the hydroxyl group. This branching has been found to be critical to the preparation of a product having the desired lubrication and oxidative stability properties. If the branching were on the same carbon as the hydroxyl group, the hydroxyl group would be a secondary one and would be very hindered and has low reactivity. As one moves the branch position away from the beta carbon, the liquidity, lubricity and metal substantivity decreases. If the branch is lower alkyl like methyl in some oxo alcohols, there is little increase in the liquidity, lubricity and metal substantivity over normal alcohols having the same number of carbons. Additionally, the oxo process gives only some beta branching ( between 1 and 28%) the guerbet process gives essentially 100% product.

Guerbet alcohols that are the reaction product of one specific raw material alcohol will result in a so called "homo-guerbet". In this case R and R' are identical. If the starting alcohols used in the guerbet reaction are of differing molecular weights a so called "hetero-guerbet" results. This type of guerbet has a mixed distribution of all possible combinations of alcohols. For this reason R and R' in the generic formula may be the same or different.

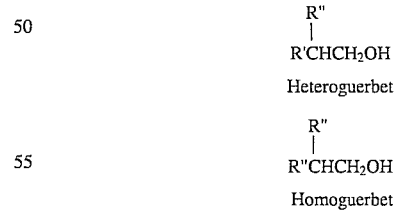

Guerbet alcohols are available commercially from Nova Molecular Technologies Janesville, Wi. They are marketed under the following commercial names:

| Example | Commercial Name | a | b |
| --- | --- | --- | --- |
| 1 | Nova Guerbet C10 | 3 | 3 |
| 2 | Nova | 4 | 4 |

Guerbet Acids

Guerbet alcohols are oxidized into acids having the same regiospecific beta branched properties. These properties present both in the acid and alcohol make products useful in the present invention.

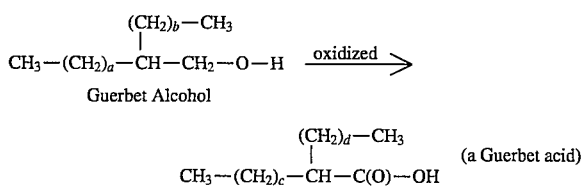

Vista Chemical practices the oxidation of guerbet alcohols commercially. The values of c and d were actually determined by analysis and are not dependant upon trade name for meaning.

| Example | Commercial Name | c | d |
|---|---|---|---|
| 8 | Isocarb 10 | 3 | 3 |
| 9 | Isocarb 12 | 4 | 4 |
| 10 | Isocarb 14 | 5 | 5 |
| 11 | Isocarb 16 | 6 | 6 |
| 12 | Isocarb 18 | 7 | 7 |
| 13 | Isocarb 20 | 8 | 8 |
| 14 | Isocarb 32 | 14 | 14 |

Isocarb is a trademark of Vista.

Di-guerbet Ester Synthesis

The esterification reaction is carried out using an excess of alcohol or acid or more typically using an equivalent of each. The esterification reaction can be carried out with or without catalyst, however when no catalyst is used the reaction times are protracted. Catalysts like benzene sulfonic acid, tin, sulfuric acid, tin salts and the like can be used. The most satisfactory catalyst is stannous oxylate.

The di-guerbet ester is prepared by the esterification reaction as shown below:

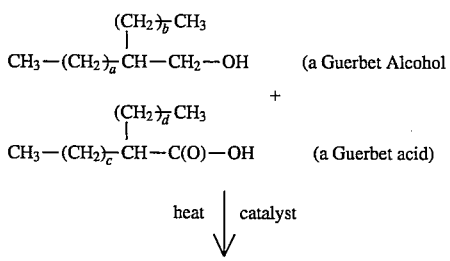

| Example | Commercial Name | a | b |
|---|---|---|---|
| 3 | Guerbet C12 Nova | 5 | 5 |
| 4 | Guerbet C14 Nova | 6 | 6 |
| 5 | Guerbet C16 Nova | 7 | 7 |
| 6 | Guerbet C18 Nova | 8 | 8 |
| 7 | Guerbet C20 Nova | 14 | 14 |
|   | Guerbet C32 |   |   |

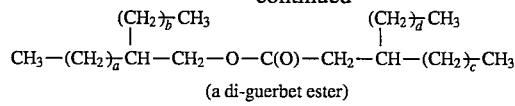

(a di-guerbet ester)

General Procedure

To the specified number of grams of guerbet alcohol (examples 1–7) is added the specified number of grams of the specified guerbet acid (Examples 8–16). Next add 0.1% stannous oxylate based upon the total weight of the batch after all ingredients have been charged, under agitation. The temperature of the mass is raised to 180–200 C. and water is stripped off as formed. The acid value and hydroxyl value drop to vanishingly small values, and the saponification value increases to theoretical. The products are clear liquids and are liquid to extraordinary temperatures. They exhibit outstanding lubrication properties and are outstanding viscosity index modifiers.

|  | Guerbet Alcohol | | Guerbet Acid | |
|---|---|---|---|---|
| Example | Example | Grams | Example | Grams |
| 15 | 1 | 157.0 | 8 | 171.0 |
| 16 | 2 | 185.0 | 9 | 199.0 |
| 17 | 3 | 213.0 | 10 | 227.0 |
| 18 | 4 | 241.0 | 11 | 255.0 |
| 19 | 5 | 269.0 | 12 | 283.0 |
| 20 | 6 | 297.0 | 13 | 311.0 |
| 21 | 7 | 465.0 | 14 | 479.0 |
| 22 | 7 | 465.0 | 8 | 479.0 |
| 23 | 6 | 297.0 | 9 | 311.0 |
| 24 | 5 | 269.0 | 10 | 283.0 |
| 25 | 4 | 241.0 | 11 | 255.0 |
| 26 | 3 | 213.0 | 12 | 227.0 |
| 27 | 2 | 185.0 | 13 | 199.0 |
| 28 | 1 | 157.0 | 14 | 171.0 |

In order to compare the compounds of the present invention to related materials the following compounds were prepared:

EXAMPLE 28

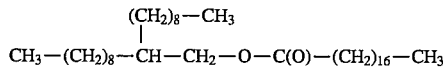

This material was prepared by the reaction of raw material example 6 with stearic acid. The resulting ester is only branched in the alcohol portion of the molecule.

EXAMPLE 30

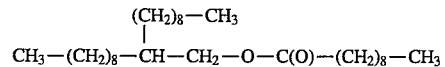

This material was prepared by the reaction of raw material example 6 with capric acid. The resulting ester is only branched in the alcohol portion of the molecule.

APPLICATIONS EXAMPLES

Lubrication Testing

The compounds of the present invention were evaluated using a standard Rothchild Tester to determine the lubrication properties. The values below indicate the lubricating efficiencies of various standard type lubricants, mono-guerbet ester. The lower the frictional value the better the lubricating properties.

FRICTIONAL PROPERTIES

| PRODUCT | DESCRIPTION (22 C) | LUBRICATION DATA* Coefficient of Friction FIBER/METAL 100 | 300 (m/min) |
|---|---|---|---|
| Example 15 | Clear oil | 0.20 | 0.21 |
| Example 22 | Clear Yellow liquid | 0.21 | 0.33 |
| Example 28 | Clear Oil | 0.22 | 0.22 |
| Example 23 | Clear Oil | 0.21 | 0.22 |
| Polyethyleneglycol tall oil Ester | Hazy Oil | 0.38 | 0.35 |
| TMP Trioleate | Clear Amber Liquid | 0.35 | 0.39 |
| Example 29 (Not of this invention) | | 0.50 | 0.52 |
| Example 30 (Not of this invention) | | 0.51 | 0.53 |

*Rothchild F Meter, Fiber; 150 denier polyester, Temperature; 72 F., Relative humidity; 60%

As can be easily seen the compounds of the present invention are good lubricants for fiber to metal lubrication. Examples 28 and 29 are beta branched only in the alcohol portion of the molecule and consequently are not as good as the materials which are beta branched in both portions of the molecule.

The additives of the present invention were formulated with a commercially available base fluid and tested in a four ball tester apparatus according to the test procedure ANSI/ASTM D-2266-67 and ANSI/ASTM D-2783-71 to determine antiwear and extreme pressure properties.

1% of the experimental compound was added to the base fluid (SITNVIS 31) under good agitation. The solutions were tested in a four ball tester at 40 kg load weight and 1,800 rpm at 170° F. The results are as follows;

Four Ball Antiwear Testing

| Load Carrying Additive | Base Fluid | Average Scar Diameter (mm) |
|---|---|---|
| None | SUNVIS 31 | 0.63 |
| Example 15 | SUNVIS 31 | 0.37 |
| Example 22 | SUNVIS 31 | 0.31 |
| Example 28 | SUNVIS 31 | 0.33 |
| Example 23 | SUNVIS 31 | 0.30 |
| Example 29 (Not of the present invention) | | 0.48 |
| Example 30 (not of the present invention) | | 0.49 |

As can be seen from the data the compounds of the present invention are outstanding lubricants. Examples 28 and 29 are beta branched only in the alcohol portion of the molecule and consequently are not as good as the materials which are beta branched in both portions of the molecule.

Four Ball Extreme Pressure Test

| Load Carrying Additive | Base Fluid | Load Wear Index | Last Nonseizure | Weld Load |
|---|---|---|---|---|
| None | SUNVIS 31 | 14 | 32 | 160 |
| Example 15 | SUNVIS 31 | 25 | 58 | 220 |
| Example 22 | SUNVIS 31 | 28 | 56 | 240 |
| Example 28 | SUNVIS 31 | 26 | 54 | 255 |
| Example 23 | SUNVIS 31 | 25 | 58 | 250 |

SUNVIS 31 is a high viscosity index, neutral petroleum oil of parafinnic base.

As can be seen from the data the compounds of the present invention are good lubricants.

I claim:

1. A di-guerbet ester conforming to the following structure:

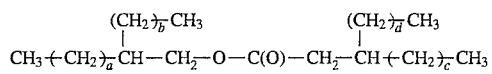

wherein a, b, c and d are independently integers ranging from 4 to 20.

2. A di-guerbet ester of claim I wherein a, b , c and d are each 4.

3. A di-guerbet ester of claim I wherein a, b, c and d are each 5.

4. A di-guerbet ester of claim 1 wherein a, b c and d are each 6.

5. A di-guerbet ester of claim 1 wherein a, b, c and d are each 7.

6. A di-guerbet ester of claim I wherein a, b, c and d are each 14.

7. A di-guerbet ester of claim 1 wherein a and b are 8 and c and d are 4.

8. A di-guerbet ester of claim I wherein a and b are 7 and c and d are 5.

9. A di-guerbet ester of claim I wherein a and b are 5 and c and d are 8.

10. A di-guerbet ester of claim I wherein a and b are 4 and c and d are 8.

* * * * *